United States Patent
Willert et al.

(10) Patent No.: US 6,340,370 B1
(45) Date of Patent: Jan. 22, 2002

(54) MODULAR SET OF AN OUTER SHELL FOR AN ARTIFICIAL HIP JOINT CUP

(75) Inventors: Hans-Georg Willert, Göttingen (DE); Kurt Bider, Winterthur (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/507,488

(22) Filed: Feb. 10, 2000

(30) Foreign Application Priority Data

Mar. 10, 1999 (EP) .............................................. 99810210

(51) Int. Cl.[7] .................................................. A61F 2/34
(52) U.S. Cl. ................................... 623/22.38; 623/22.21
(58) Field of Search ........................... 623/22.21, 22.32, 623/22.34, 22.35, 22.36, 22.37, 22.38, 22.42

(56) References Cited

U.S. PATENT DOCUMENTS 5,702,477 A   12/1997   Capello

FOREIGN PATENT DOCUMENTS

| EP | 0501207 A1 | 9/1992 |
|----|------------|--------|
| EP | 0605368 A1 | 7/1994 |
| EP | 0846453 A2 | 6/1998 |

*Primary Examiner*—David J. Isabella
(74) *Attorney, Agent, or Firm*—Townsend and Townsend and Crew LLP

(57) ABSTRACT

Modular set of an outer shell (1) for an artificial hip joint pan, comprising a shell-shaped outer part (2) and an anchoring aid (7) which is designed as a lug (3, 4), a spike (5) or a hook (6), with the shell-shaped outer part (2) having an end surface (2*a*) at its equator with bores (2*b*), and with each anchoring aid (7) having a securing part (3*a*, 4*a*, 5*a*) which is designed to be matched with respect to the end surface (2*a*) in such a manner that the securing part (3*a*, 4*a*, 5*a*) can be secured at the shell-shaped outer part (2) by means of a screw (6) which engages in the bore (2*b*).

12 Claims, 2 Drawing Sheets

MODULAR SET OF AN OUTER SHELL FOR AN ARTIFICIAL HIP JOINT CUP

Figure 1:
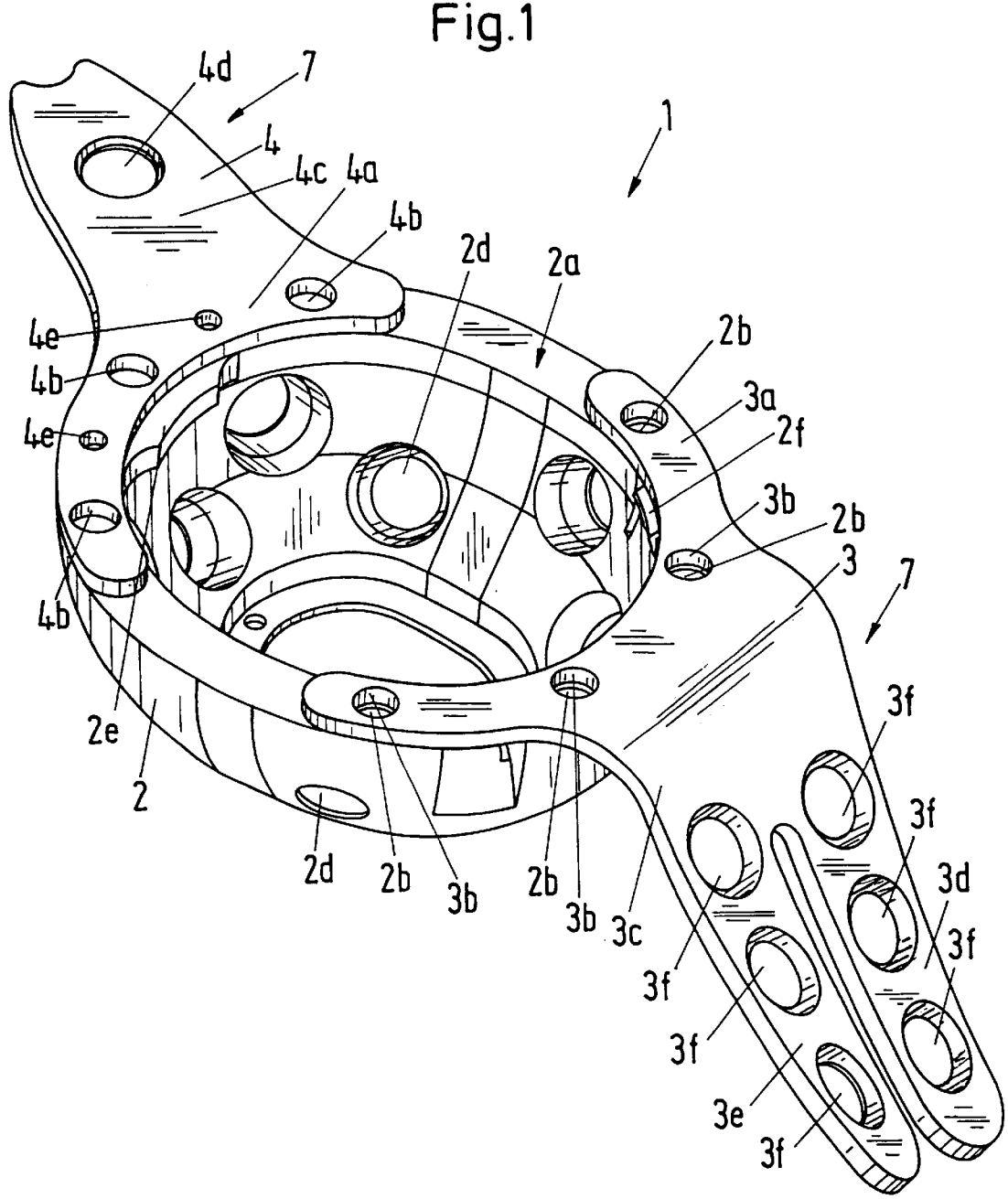

The invention relates to a modular set of an outer shell for an artificial hip joint pan in accordance with the preamble of claim 1.

An outer shell for an artificial hip joint pan which consists of a hemispherical shell and lug parts which are projectingly arranged at its equatorial edge is known from the document EP-A-0 563 503. An outer shell of this kind is for example used when the acetabulum is damaged or strongly degenerate at the location to be carried, which is often the case in particular in revisions of implanted artificial joints. The lug parts are matched to the shape of the "os ilium" bone or the "os ischii" bone respectively during the implanting through plastic deformation and are afterwards anchored in a region capable of carrying by means of bone screws, so that the outer shell is firmly secured at the pelvic bone.

Disadvantageous is the fact that a large number of outer shells of different sizes is required. Disadvantageous in the known outer shell is in addition the fact that a relatively large opening at the operation field is required for the implanting. In addition the matching of the shape of the lug parts to the shape of the pelvic bone is difficult and complicated.

The object of the present invention is to propose an outer shell which is more economical and simpler to implant.

This object is satisfied with a modular set of an outer shell having the features of claim 1.

Subordinate claims 2 to 9 relate to further advantageous embodiments of the outer shell.

The object is satisfied in particular with a modular set for an outer shell comprising a shell-shaped outer part and an anchoring aid which is designed as a lug, a spike or a hook, with the shell-shaped outer part having at its equator an end surface with bores, and with each anchoring aid having a securing part which is designed to be matched with respect to the end surface in such a manner that the securing part can be secured at the shell-shaped outer part by means of screws which engage in the bore.

The modular construction of the outer shell in accordance with the invention has the advantage that the modular set comprises a plurality of differently shaped, shell-shaped outer parts and/or anchoring aids so that it is left up to the surgeon to decide during the operation which shell-shaped outer part and/or which anchoring aids are best suited for the anchoring in accordance with the state and the anatomy of the pelvic bone. Since the outer shell can be assembled on site in the operation field, the opening of the operation field can be kept small, which for example has a protective effect on the soft parts. After the introduction of the shell-shaped outer part a suitable lug can be selected and applied to the pelvic bone in the operation field. The lug advantageously has a shape which is pre-formed to the anatomical shape of the pelvic bone. Should it turn out in the matching of the lug to the pelvic bone that their mutual shapes do not agree ideally, then the lug can be removed again from the operation field and be reshaped outside the operation field with suitable tools. As far as required the process of the laying on of the lug at the pelvic bone and the reshaping can be repeated a plurality of times. As soon as the lug has the desired anatomical shape the lug can be firmly connected to the shell-shaped outer part with the help of a screw. The ideal choice of the lug shape, the lug size and their kind of anchoring in the pelvic bone is of importance for the reliable, long term anchoring of the outer shell, in particular when the pelvic bone has larger defects such as holes. In addition the shell-shaped outer part can also be chosen in accordance with the defect of the pelvic bone. For example round or ovally designed outer parts are available to be chosen from. It proves for example to be particularly advantageous in the event of a large hole in the pelvic bone to choose a correspondingly large outer part in order to fill the hole with the implant, which stabilises the bone.

Should it turn out during the implanting that the lug is not suitable or additional anchoring aids are required for the fixing of the outer part, then for example a spike or a hook can be used as a further anchoring aid.

Figure 2:
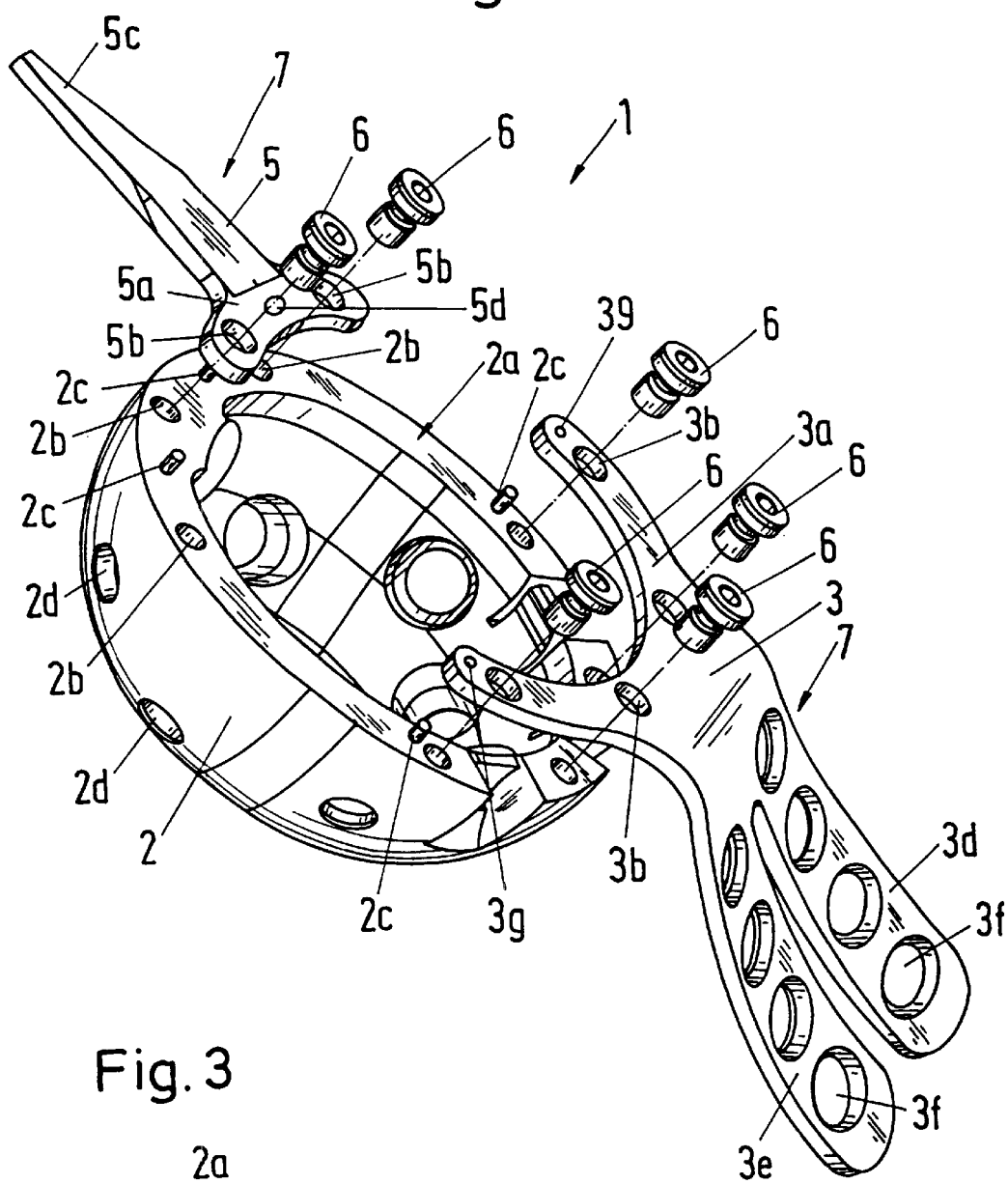
Figure 3:
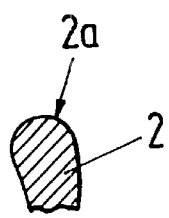

The invention will be described with reference to a plurality of exemplary embodiments. Shown are:

FIG. 1 a perspective view of an assembled outer shell;
FIG. 2 a perspective view of a further outer shell;
FIG. 3 a partial view of a cross-section through the outer shell.

FIG. 1 shows an outer shell 1 which consists of a shell-shaped outer part 2 as well as two anchoring aids 7 which are releasably connected to the outer part 2 and are designed as lugs 3, 4. The shell-shaped outer part 2 has at its equator an end surface 2a which is designed as a planar surface in the illustrated exemplary embodiment. The end surface 2a has a plurality of bores 2b which are distributedly arranged over their periphery and which have an inner thread for the reception of a screw 6. The lugs 3, 4 each comprise a securing part 3a, 4a which is intended for securing at the end surface 2a, with the securing part 3a, 4a having apertures 3b which are executed as bores and which are arranged to cover the same area as the bores 2b. The securing part 3a, 4a can, as is illustrated in FIG. 2, be firmly connected to the shellshaped outer part 2 by means of screws 6 which engage into the bore 2b extending through the aperture 3b. FIG. 1 shows the shell-shaped outer part 2 and the lugs 3, 4 in the firmly connected position, with the screws 6 not being illustrated for the sake of clarity.

The lug 3 is formed in a single piece and consists of a securing part 3a, a transition part 3c which adjoins at it and which opens into two tongue-shaped lug parts 3d, 3e which extend substantially parallel to one another. The lug parts 3d, 3e have apertures 3f through which bone screws can be introduced for the anchoring in the pelvic bone. The lug 3 is pre-shaped in such a manner that at least the lug parts 3d, 3e have a shape which is matched approximately corresponding to the anatomy of the pelvic bone. The lug 4 is likewise formed in a single piece and consists of a securing part 4a, which has apertures 4b for the reception of a screw 6 and apertures 4e for the reception of a cam 2c, as well as a lug part 4c with aperture 4d for a bone screw. The lug 4 is designed to extend planarly.

The outer part 2 is designed to be oval in the illustrated embodiment. The outer part 2 has apertures 2d through which where appropriate bone screws are introducible for the anchoring in the pelvic bone. The outer part 2 comprises in addition in the illustrated exemplary embodiment a cam 2e and snap parts 2f which serve for the holding of a non-illustrated inner shell.

FIG. 2 shows a further exemplary embodiment of an outer shell 1 with anchoring aids 7 and screws 6. Identical reference numerals designate the same objects as were already described in FIG. 1. Projecting cams 2c are arranged at the end surface 2a in addition to the bores 2b. The securing part 3a of the lug 3 has in addition to the apertures 3b which are provided for the screws 6 two bores 3g which are arranged in such a manner that they each surround a cam 2c when the lug 3 lies on the end surface 2a. The cams 2c serve on the one hand as an aid for the correct positioning of the lug 3 during the lying in contact on the end surface 2a. In addition the cams 2c serve for taking up the thrust tensions which are caused by the lug 3. A further embodiment of an anchoring aid 7 is executed as a spike 5 which consists of a securing part 5a and a spike part 5c. The securing part 5a has two apertures 5b, through each of which a screw 6 can be passed for the securing at the shell-shaped outer part 2. The securing part 5a also has an aperture 5d which is intended for the reception of the cam 2c. Two projecting cams 2c are arranged at the end surface 2a lying opposite to the spike 5, with the spike being connectable to the shell-shaped outer part 2 in a manner which is selectable such that one of the cams 2c comes to lie in the aperture 5d. The spike part 5c is centeredly arranged with respect to the two apertures 5b. The spike part 5c could also extend asymmetrically, overhanging to the one side with respect to the securing part 5a. This asymmetrical spike 5 can be designed in such a manner that it can be secured in two different positions at the end surface 2a, namely rotated by in each case 180 degrees about the axis of the spike part 5c.

The cam can also be arranged projectingly at the securing part 3a, 4a, 5a, with it being required to provide a corresponding cut-out in the end surface 2a for the reception of the cam.

The shell-shaped outer part 2 and the anchoring aids 7 are preferably manufactured of titanium or a titanium alloy.

The modular set in accordance with the invention preferably comprises a plurality of shell-shaped outer parts 2 of different sizes or, respectively, also differently shaped outer parts 2, for example with round or ovally extending end surfaces 2a. In addition the modular set comprises a plurality of differently shaped anchoring aids 7, which all have a securing part 3a, 4a, 5a in order to connect the anchoring aid 7 firmly to the shell-shaped outer part 2 at the end surface 2a. The anchoring aids 7 can for example have tongues of different length or be differently shaped anatomically. In addition the anchoring aids 7 can also be designed for an outer shell 1 which is to be implanted on the left or on the right. Preferably screws 6, but also other means which effect a connection, are suitable for a connection. The end surface 2a could also have a different shape and, as is for example illustrated in FIG. 3 with a piece cut out of a radial section through the outer part 2, have a semicircular shape. The securing part 3a, 4a, 5a would naturally have to have a counter-surface which extends in a manner which is matched to the shape of the end surface 2a.

During the implanting of the outer shell 1 the surgeon can assemble the suitable components in accordance with the state of the pelvic bone. First a suitable shell-shaped outer part 2 is selected and, if required, the pelvic bone is prepared in such a manner that the shell-shaped outer part 2 can be arranged in the anatomically correct position in the pelvic bone. Thereupon those anchoring aids 7 are selected from the large number of available anchoring aids 7 which ensure a reliable anchoring of the shell-shaped outer part 2 in the pelvic bone. At least one of the anchoring aids 7 illustrated in FIGS. 1 and 2 is used, preferably however two. The lug 3 has an anatomically pre-shaped extent. The surgeon, for example when the outer part 2 is inserted in the pelvic bone, lays the lug 3 in contact at the end surface 2a and checks whether the shape of the lug parts 3d, 3e approximately agrees with the anatomical shape of the pelvic bone. If the deviation is too great the lug 3 is removed again and reshaped outside the body with the help of a tool. The lug 3 is again laid in contact at the end surface 2a and either firmly connected to the outer part 2 with screws 6 or removed again and reshaped. An advantage of the projecting cams 2c is to be seen in that during this adaptation the lug 3 latches into the cams 2c and thus the mutual position of the lug 3 and the end surface 2a is precisely defined. It can also prove advantageous to use additional aids. Instead of the cams 2c, which are firmly connected to the outer part 2c, for example releasable cams or a short bar could also be screwed into the bore 2b of the end surface 2a, with the bores 3b of the securing part 3a being introduced in these cams or this bar respectively so that the lug 3 is reliably guided with respect to the end surface 2a or the outer part 2 respectively. After the lug 3 is secured with a screw 6 the cam or the bar respectively can be removed and a screw 6 likewise introduced at this location.

The spike 5 is usually hammered in into the pelvic bone for the anchoring. In this the spike 5 is first hammered in in order afterwards to be firmly secured to the outer part 2. It is however also possible to first connect the spike 5 firmly to the outer part 2 and afterwards to hammer the spike 5 in together with the outer part 2.

The anchoring aid 7 can also be designed as a hook which has a securing part 3a, 4a, 5a.

The apertures 3b, 4b, 5b of the securing part 3a, 4a, 5a could be also designed to be elongately extending in the direction of the course of the end surface 2a in order to enable a slight relative movement between the outer part 2 and the anchoring aid 7 in the direction of the course of the end surface 2a when the screw 6 is inserted into the bore 2b. This relative movement is subsequently prevented through a firm tightening of the screw 6.

What is claimed is:

1. A modular set of an outer shell (1) for an artificial hip joint cup and anchoring parts (7), comprising:

an oval elongate hemispheric shell (2) having a larger hemispheric dimension at elongate ends in a preferred direction;

a frontal surface (2a) defined in an equatorial plane of the oval elongate hemispheric shell (2);

threaded bores (2b) provided in the frontal surface (2a);

one or more screws (6) for engaging the threaded bores (2b);

snap parts (2f) arranged in corresponding recesses provided in the frontal surface (2a), the snap parts (2f) being placed proximate to one of the elongate ends of the oval elongate hemispheric shell (2);

one or more anchoring parts (7) which are selected from the group consisting of a lug (3, 4), a spike (5) and a hook;

each anchoring part (7) having a securing part (3a, 4a, 5a) designed to match the frontal surface (2a);

bores (3b, 4b, 5b) defined by the securing parts (3a, 4a, 5a), the bores (3b, 4b, 5b) corresponding to threaded bores (2b) provided in the frontal surface (2a) in such a manner that the securing part (3a, 4a, 5a) can be secured at the oval elongate hemispheric shell (2) by means of the one or more screws (6) which engage in the bore (2b); and, at least one anchoring part (7) being designed and arranged in such a manner that its securing part (3a, 4a, 5a) bridges the recesses and the corresponding snap parts (2f).

2. The modular set of an outer shell (1) for an artificial hip joint cup and anchoring parts (7) according to claim 1 and wherein: the frontal surface (2a) has a planar surface.

3. The modular set of an outer shell (1) for an artificial hip joint cup and anchoring parts (7) according to claim 1 and wherein:

the one or more anchoring parts (7) is a lug (3, 4) consisting of a securing part (3a, 4a) with a tongue-shaped lug part (3d, 3e, 4c).

4. The modular set of an outer shell (1) for an artificial hip joint cup and anchoring parts (7) according to claim 3 and wherein:

the tongue-shaped lug part (3d, 3c, 4c) is shaped substantially to conform to the anatomy of the pelvic bone.

5. The modular set of an outer shell (1) for an artificial hip joint cup and anchoring parts (7) according to claim 3 and wherein:

the lug (3, 4) has at least two lug parts (3d, 3e) which extend substantially parallel to one another.

6. The modular set of an outer shell (1) for an artificial hip joint cup and anchoring parts (7) according to claim 3 and wherein:

the lugs (3, 4) are deformable.

7. The modular set of an outer shell (1) for an artificial hip joint cup and anchoring parts (7) according to claim 1 and wherein:

the frontal surface (2a) has a projecting cam (2c) and the securing parts (3a, 4a, 5a) have a cut-out (3g, 5b) for the reception of the cam (2c).

8. The modular set of an outer shell (1) for an artificial hip joint cup and anchoring parts (7) according to claim 1 and wherein:

the anchoring parts (7) include titanium.

9. A modular set of an outer shell (1) for an artificial hip joint cup and anchoring parts (7) according to claim 1 and wherein:

the oval elongate hemispheric shell (2) is provided with at least four threaded bores (2b) provided in the frontal surface (2a) and with three snap parts (2f) each arranged in a recess provided in the frontal surface (2a); and, the anchoring part (7) has at least four screws (6) causing the securing part (3a, 4a, 5a) to be secured to the oval elongate hemispheric shell (2) by means of four screws (6) which engage in the four threaded bores (2b).

10. The modular set of an outer shell (1) for an artificial hip joint cup and anchoring parts (7) according to claim 1 and wherein:

the oval elongate hemispheric shell (2) is selected from a plurality of differently sized and shaped oval elongate hemispheric shells (2).

11. The modular set of an outer shell (1) for an artificial hip joint cup and anchoring parts (7) according to claim 1 and wherein:

the anchoring parts (7) are selected from a plurality of differently sized and shaped anchoring parts (7).

12. The modular set of an outer shell (1) for an artificial hip joint cup and anchoring parts (7) according to claim 1 and wherein:

the oval elongate hemispheric shell (2) is configured for the holding of an inner shell.

* * * * *